United States Patent
Löber et al.

(10) Patent No.: US 7,256,312 B2
(45) Date of Patent: Aug. 14, 2007

(54) METHOD FOR PRODUCING AMINOALKOXY BENZYLAMINES AND AMINOALKOXY BENZONITRILES AS INTERMEDIATES

(75) Inventors: Oliver Löber, Freimersheim (DE); Christoph Benisch, Mannheim (DE); Klaus Ebel, Lampertheim (DE); Johann-Peter Melder, Böhl-Iggelheim (DE)

(73) Assignee: BASF Aktiengesellschaft, Ludwigshafen (DE)

( * ) Notice: Subject to any disclaimer, the term of this patent is extended or adjusted under 35 U.S.C. 154(b) by 286 days.

(21) Appl. No.: 10/522,614

(22) PCT Filed: Jul. 18, 2003

(86) PCT No.: PCT/EP03/07871

§ 371 (c)(1),
(2), (4) Date: Jan. 31, 2005

(87) PCT Pub. No.: WO2004/013082

PCT Pub. Date: Feb. 12, 2004

(65) Prior Publication Data

US 2005/0256340 A1 Nov. 17, 2005

(30) Foreign Application Priority Data

Aug. 1, 2002 (DE) ................. 102 35 312

(51) Int. Cl.
*C07C 209/48* (2006.01)
*C07C 253/30* (2006.01)
(52) U.S. Cl. ........................ 564/415; 558/422
(58) Field of Classification Search ............... 564/415; 558/422
See application file for complete search history.

(56) References Cited

U.S. PATENT DOCUMENTS

| | | | |
|---|---|---|---|
| 2,626,261 A * | 1/1953 | Clinton et al. | 546/230 |
| 2,642,436 A * | 6/1953 | Clinton et al. | 546/230 |
| 2,642,437 A * | 6/1953 | Clinton et al. | 546/230 |
| 2,879,293 A | 3/1959 | Goldberg et al. | |
| 3,193,579 A | 7/1965 | Goldberg et al. | |
| 3,959,338 A * | 5/1976 | Koppe et al. | 558/422 |
| 5,852,035 A | 12/1998 | Pamukcu et al. | |
| 5,874,625 A * | 2/1999 | Elsasser | 564/490 |
| 5,990,139 A | 11/1999 | Yano et al. | |

FOREIGN PATENT DOCUMENTS

| | | |
|---|---|---|
| BE | 853789 | 4/1977 |
| DE | 32 33 828 | 3/1984 |
| EP | 0 306 827 B1 | 3/1989 |
| EP | 0 758 653 A1 | 2/1997 |
| FR | 2 549 828 | 2/1985 |
| GB | 924961 | 2/1960 |
| GB | 2 060 622 A | 5/1981 |
| WO | WO-02/076925 A2 | 10/2002 |

OTHER PUBLICATIONS

Pharm. Chem. J., Lerner, O.M. et al., Bd. 7, 1969, Seite 382-383, XP 00109133.
Bull. Soc. Chim. Fr. BD 5, Nr. 12, 1945, Seite 1050-1055, XP 000116094.
Journal of Medicinal Chemistry, American Chemical Society. Washington, US, Bd. 14, Nr. 9, 1971, Seite 836-842.
Kmonicek et al., Collect. Czech. Chem. Commun. 1089, 54, 1721-1733.
G. Uray und I. Kriessmann, Synthesis, 679-681 (1984).
Yurugi et al. Chem. Pharm. Bull. 1973, 21, Seiten 1641-1659.

* cited by examiner

*Primary Examiner*—Brian Davis
(74) *Attorney, Agent, or Firm*—Connolly Bove Lodge & Hutz LLP

(57) ABSTRACT

The invention relates to a process for preparing 4-[aminoalkoxy]benzylamines of the general formula (I)

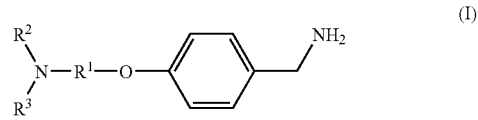

by catalytically hydrogenating 4-[aminoalkoxy]benzonitriles of the general formula (II)

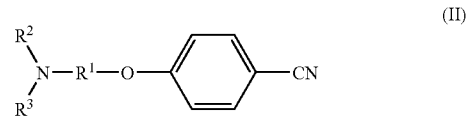

where, in the compounds of the general formulae I and II, $R^1$ is $C_1$-$C_8$-alkylene, $R^2$ and $R^3$ are each independently $C_1$-$C_8$-alkyl or are joined to give a ring which may additionally contain a heteroatom, which comprises carrying out the hydrogenation at elevated pressure and elevated temperatures. The invention further relates to a process for preparing the intermediate (II).

17 Claims, No Drawings

METHOD FOR PRODUCING AMINOALKOXY BENZYLAMINES AND AMINOALKOXY BENZONITRILES AS INTERMEDIATES

CROSS REFERENCE TO RELATED APPLICATION

The present application is a National Stage application of PCT/EP2003/007871, filed Jul. 18, 2003, which claims priority from Germany Patent Application No. DE 102 35 312.3, filed Aug. 1, 2002.

The present invention relates to an improved process for preparing aminoalkoxybenzylamines I by catalytically hydrogenating aminoalkoxybenzonitriles II. The invention further relates to an improved process for preparing the aminoalkoxybenzonitriles II from the aminoalcohols III and 4-halobenzonitrile.

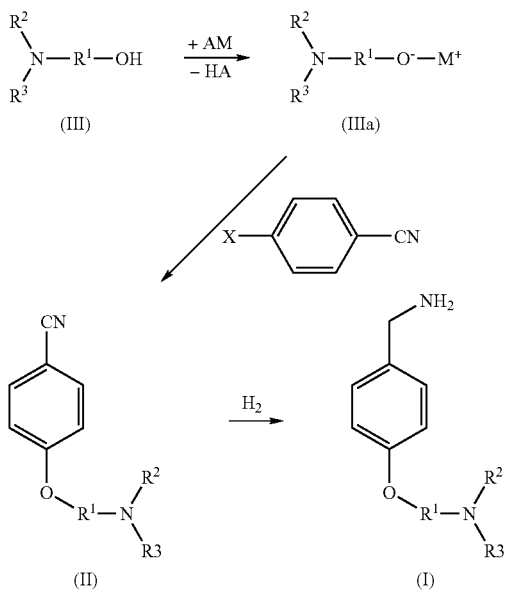

In the compounds of the general formulae I, II and III, $R^1$ is $C_1$-$C_8$-alkylene; $R^2$ and $R^3$ are each independently $C_1$-$C_8$-alkyl or are joined to give a ring which may additionally contain a heteroatom; M is an alkali metal or an alkaline earth metal and A is hydride, $C_1$-$C_4$-alkyl, hydroxyl or $C_1$-$C_4$-alkoxy; X is chlorine or bromine. In the case of the alkaline earth metal hydrides, each HA is —$H_2$.

Aminoalkoxybenzylamines of the formula I are important intermediates in the synthesis of biologically active substances, for example active pharmaceutical ingredients.

In Author's Certificate No. 218194; Byull. Izobretenii, No. 17 (1968) O. M. Lerner and F. Yu. Rachinskii describe the catalytic hydrogenation of 4-[2-(dimethylamino)ethoxy] benzonitrile with hydrogen in the presence of Raney nickel at from 16 to 20° C. under atmospheric pressure. However, the 70 to 73% yields of (III) achieved based on (II) are unsatisfactory.

O. M. Lerner et al. in Pharm. Chem. J. 1969, 7, 382-383 describe the heterogeneous-catalyzed hydrogenation of 4-[2-(dimethylamino)ethoxy]benzonitrile with hydrogen in the presence of Raney nickel in anhydrous ethanol at room temperature and atmospheric pressure. After a hydrogenation period of from 10 to 20 hours, 84% of the desired product, based on (II), are obtained. However, a distinct shortening in the hydrogenation period and a higher yield are required for industrial application.

U.S. Pat. No. 2,879,293 discloses the preparation of (I) by reductive amination of 4-[2-(dimethylamino)ethoxy]benzaldehyde in the presence of ammonia in ethanol at 80° C. and 69 bar over Raney nickel. However, the yields achieved are not disclosed. A disadvantage is the use of the starting material 4-[2-(dimethylamino)-ethoxy]benzaldehyde which, according to the disclosed process, is prepared from p-hydroxybenzaldehyde and the highly toxic 2-chloroethyldimethylamine.

U.S. Pat. No. 3,193,579 likewise discloses a process for preparing 4-[2-(dimethylamino)ethoxy]benzylamine starting from 4-[2-(dimethylamino)ethoxy]benzaldehyde in the presence of ammonia in ethanol at 160° C. and 21 bar over a supported palladium catalyst (10% of Pd on calcium carbonate). As in U.S. Pat. No. 2,879,293, a disadvantage is the use of 4-[2-(dimethylamino)ethoxy]-benzaldehyde and also the use of an expensive noble metal catalyst having a high noble metal content.

EP 0306827 discloses a process for preparing 4-[2-(dimethylamino)ethoxy]benzylamine from 4-[2-(dimethylamino)-ethoxy]benzaldehyde by oximating with hydroxylamine hydrochloride in ethanol. This initially gives benzaldoxime hydrochloride from which benzaldoxime is released by treating with potassium carbonate/water and obtained by crystallization (95% yield). Afterwards, the heterogeneously catalyzed hydrogenation with hydrogen over Raney nickel in methanol is effected in the presence of ammonia at 30° C. and 49 bar. The yield of the desired product achieved in the hydrogenation is not disclosed. In JP 01100159 belonging to the patent family, a hydrogenation yield of 93% based on the benzaldoxime used is achieved. Over and above the disadvantages described in the case of U.S. Pat. No. 2,879,293, the process becomes costly and inconvenient as a result of the two-stage preparation and the necessary crystallization of the benzaldoxime, and thus uneconomic.

FR 2549828 discloses a multistage process for preparing 4-[2-(dimethylamino)ethoxy]benzylamine starting from phenol. Reaction of phenol with ethylenechlorohydrin initially delivers 2-phenoxyethanol which is reacted with thionyl chloride to give 2-phenoxyethyl chloride. After distilling this intermediate, it is reacted with acetamide and paraformaldehyde and then treated with mineral acid to give N-(2-chloroethoxybenzyl)acetamide. Reaction with dimethylamine then leads to N-[2-(dimethylamino)-ethoxy] acetamide, from which the desired product is released by acid hydrolysis. The process disclosed which has 6 separate process steps and an overall yield of 50% based on the phenol used is uneconomic.

Processes for preparing 4-aminoalkoxybenzonitriles (II) are likewise known:

BE 853789 discloses a process for alkoxylating aryl compounds of the general formula X-A-$Z_n$ where X=halogen, Z is an electron-withdrawing group, in particular $NO_2$, and n=1-2. The reaction is effected with an alcohol in the presence of sodium hydroxide and tetrabutylammonium bromide, optionally in chlorobenzene as solvent, with the substitution of the halogen atom from X-A-$Z_n$. The adduced examples use exclusively nitroaromatics as substrates.

DE 3233828 discloses two processes for preparing aryloxyalkylamines, either (a) by reacting a phenoxyalkyl halide of the formula $Y_m$—Ar—O—$(CH_2)_n$-Hal (where $Y_m$ may, inter alia, be CN, m=1-3, n=5-12) with a secondary amine $R^1R^2NH$ or (b) by reacting aminoalkyl halides of the formula $Hal-(CH_2)_n-NR^1R^2$ with the alkali metal salt of a phenol of the formula $Y_m-Ar-OH$.

GB 924961 discloses a process for preparing (II) by reacting p-cyanophenol with 2-chloroethyldimethylamine in toluene in the presence of sodium hydroxide. The yield achieved is not disclosed. A disadvantage of this process is the use of the toxic 2-chloroethyldimethylamine.

Yurugi et al. in Chem. Pharm. Bull. 1973, 21, 1641-1659 describe the reaction of p-cyanophenol with 2-chloroethyldiethylamine. As in GB 924961, the use of the toxic 2-chloroethyldialkylamine is to be regarded as disadvantageous.

Kmoníček et al. in Collect. Czech. Chem. Commun. 1989, 54, 1721-1733 describe a method for preparing (II) by reacting 4-[2-(dimethylamino)ethoxy]benzaldehyde with nitroethane by heating with ammonium acetate in acetic acid. A disadvantage of an industrial process is the handling of the explosive nitroethane and the low yield of (II) of only 40% based on 4-[2-(dimethylamino)ethoxy]benzaldehyde.

G. Uray and I. Kriessmann in Synthesis, 679-681 (1984) further describe the preparation of alkylaryl ethers by reacting alcohols with 4-chlorobenzonitrile in the presence of potassium hydroxide in dimethyl sulfoxide, although a nitrile group is hydrolyzed.

It is an object of the present invention to provide a simple, economic process for preparing 4-[aminoalkoxy]-benzylamines (I) which overcomes the disadvantages of the prior art, dispenses with the use of toxic reagents and delivers the desired product in high yields.

We have found that this object is achieved by a process for preparing 4-[aminoalkoxy]benzylamines (I) by catalytically hydrogenating 4-[aminoalkoxy]benzonitriles (II), which comprises carrying out the hydrogenation at elevated pressure and elevated temperatures.

A process has also been found for preparing 4-[aminoalkoxy]benzonitriles (II), which comprises initially converting an aminoalcohol (III) to an alkali metal salt and then reacting it with 4-halobenzonitrile.

In the compounds of the general formulae I, II and III, $R^1$ is $C_1$-$C_8$-alkylene, preferably ethylene; $R^2$ and $R^3$ are each independently $C_1$-$C_8$-alkyl, preferably methyl or ethyl, or are joined to give a saturated 5- or 6-membered ring which may additionally contain a heteroatom, so that $NR^2R^3$ may be pyrrolidine, piperidine, piperazine or morpholine.

The invention relates in particular to a process for preparing 4-[2-(dimethylamino)ethoxy]benzylamine (I) from 4-chlorobenzonitrile via the intermediate 4-[2-(dimethylamino)ethoxy]benzonitrile (II).

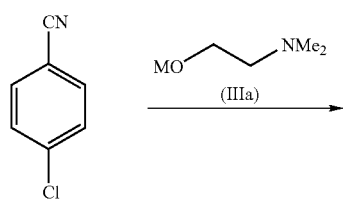

(IIIa)

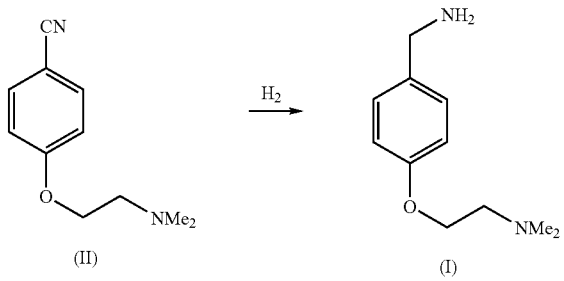

4-Chlorobenzonitrile is initially coupled with an alkali metal salt of the aminoalcohol (III) to obtain 4-[2-(dimethylamino)ethoxy]benzonitrile (II).

In a first step, a salt of the aminoalcohol is prepared with the aid of a base AM. The bases used are advantageously alkali metal alkyl compounds, alkali metal hydrides or alkali metal alkoxides, e.g. BuLi, NaH, LiH, NaOMe or NaOEt. Alkaline earth metal hydrides, e.g. calcium hydride, or alkaline earth metal hydroxides are also suitable. It is also possible to use sodium hydroxide or potassium hydroxide, as long as water is distilled out of the reaction mixture.

Particularly preferred bases are NaOMe and NaOEt. In these cases too, methanol or ethanol is distilled off. When these bases are used, it is recommended to carry out the reaction under protective gas such as nitrogen or argon.

In a second step, the isolated alkali metal salt of the aminoalcohol or advantageously a solution formed in situ of the alkali metal salt is reacted with p-chlorobenzonitrile in a suitable solvent at temperatures between 100 and 140° C., preferably at temperatures between 125 and 135° C., the amounts of alkali metal salt used being such that there is a small excess of from 1.00 to 1.5 equivalents per equivalent of 4-chlorobenzonitrile. Preference is given to using a small excess, i.e. at least 1.05 equivalents, or more.

The solvents for the coupling reaction are advantageously strongly polar, high-boiling, aprotic solvents, e.g. NMP, DMF or DMSO. Ethers or open-chain polyethers, for example diphenyl ether, diethyl glycol, dibutyl glycol or dimethyl glycol are also suitable. Equally, the N,N-dimethylaminoethanol used as a reaction partner may be used in excess and take over the function of a solvent.

In order to shift the equilibrium very substantially to the side of the salt, care must be taken that the alcohol or the water is very substantially distilled off, in order to prevent the formation of by-products, for example methoxy derivatives.

The product of value is recovered extractively from the reaction mixture after aqueous workup. The extractants used are preferably solvents such as ethers, esters, or aliphatic or aromatic hydrocarbons. Preference is given to using ethyl acetate, tert-butyl acetate, xylene and toluene, in particular ethyl acetate and toluene. Mesitylene and decalin are also suitable. When toluene or xylene is used as the extractant, removal, before adding water, of alkali metal chloride precipitating out in the reaction may be dispensed with. The workup may then be effected by distilling the reaction product under a reduced pressure of from 1 to 20 mbar. For example, a purification by distillation under a reduced pressure of from 5 to 10 mbar delivers 4-[2-(dimethylamino) ethoxy]benzonitrile (II) in yields of up to 85%. When toluene or xylene is used, the organic phase may also be fed directly to the hydrogenation without distillation.

In the second process stage, the 4-[aminoalkoxy]benzonitrile (II) is reacted with hydrogen over a catalyst to obtain 4-[aminoalkoxy]benzylamines (I) at elevated pressure and elevated temperature.

The active catalyst composition of the catalysts used in the process according to the invention comprises from 2 to 100% by weight of at least one element or at least one compound of an element of group VIII of the Periodic Table, i.e. from the group consisting of Fe, Ru, Os, Co, Rh, Ir, Ni, Pd and Pt. Particular preference is given to cobalt and nickel, especially Raney cobalt and Raney nickel.

The catalysts may be used as unsupported catalysts or in supported form. When supported catalysts are used, the proportion of the support in the total mass of the catalyst (active composition+support) is generally from 10 to 98% by weight.

The supports used may be any known suitable support, for example activated carbon, silicon carbide or metal oxides. Among the metal oxides, preference is given to using aluminum oxide, silicon dioxide, titanium dioxide, zirconium dioxide, zinc oxide, magnesium oxide or their mixtures, each of which may optionally be doped with alkali metal oxides and/or alkaline earth metal oxides. The supports may be used in any desired form, for example as extrudates (in the shape of strands), pellets, tablets, monoliths, weaves, knits, or in powder form. The supported catalysts may be prepared by the generally known processes.

The process according to the invention is carried out at temperatures of from 50 to 250° C., preferably from 60 to 110° C., and pressures of from 5 to 350 bar, preferably from 5 to 200 bar, more preferably from 10 to 80 bar, continuously or preferably batchwise in pressure apparatus such as tubular reactors or preferably in an autoclave. The pressure is preferably the hydrogen pressure in the autoclave.

The process according to the invention can be carried out without solvent or preferably in solvents such as alcohols, ethers, cyclic ethers, aliphatic hydrocarbons or aromatic hydrocarbons. Preference is given to using methanol, tetrahydrofuran or toluene, in particular methanol or toluene. The nitrile (II) used may be dissolved in the solvent. The solvent may also be fed to the reactor separately at any desired point. When a solvent is used, the concentration of nitrile (II) in the solvent is from 5 to 80% by weight (based on the sum of nitrile and solvent), preferably from 5 to 50% by weight, more preferably from 20 to 50% by weight.

In one embodiment of the process according to the invention, the hydrogenation is effected in the presence of ammonia. The ammonia content is generally from 1 to 50 mol, preferably from 2 to 20 mol, of ammonia per mole of the nitrile to be hydrogenated.

The reaction duration may be judged via the hydrogen flow, and the reaction may be regarded as complete when no more hydrogen flow takes place, i.e. no more hydrogen has to be injected in order to keep the pressure constant. The progress of the reaction may also be checked by gas chromatography analysis of samples of the reaction mixture. A further possibility is offered by infrared measurements of the progress of the reaction via the disappearance of the nitrile band.

The process according to the invention allows the simple and inexpensive preparation of aminoalkoxybenzylamines and also of the intermediate II in good yields. Surprisingly, no significant core hydrogenation of the aromatic occurs. It was also surprising that the catalyst could be recycled more than once into the reaction, even though this is normally problematic in the case of nitrile hydrogenations owing to deactivation of the catalyst.

It is also advantageous that the preparation of the intermediate II avoids hydrolysis of the nitrile group.

The invention is illustrated by the examples which follow.

EXAMPLE 1

660 ml of N,N-dimethylaminoethanol were initially charged with stirring at RT in a four-neck glass flask under an argon atmosphere. 144.4 g of 30% NaOMe solution (in MeOH) were added dropwise within 45 min. The contents of the flask were heated to 130° C. for 3 h and MeOH was distilled off. Afterwards, a solution of 91.8 g of p-chlorobenzonitrile in 460 ml of dimethylaminoethanol was added dropwise at RT within 45 min. The contents of the flask were then stirred at 130° C. for 4 h. The solid formed (predominantly NaCl) was then filtered off with suction at RT and the filtrate was concentrated on a rotary evaporator at 70° C. and 15 mbar. The residue was then extracted using 200 ml of water and 400 ml of ethyl acetate. The aqueous phase was again extracted with 200 ml of ethyl acetate and the combined organic phases were dried over $MgSO_4$. The solvent was then removed on a rotary evaporator and the residue distilled via a column. At about 160° C. and 5 mbar, 4-[2-(dimethylamino)ethoxy]-benzonitrile was obtained in a yield of 69.2% (89.2 g) having a GC purity of >97% (percentage area).

EXAMPLE 2

600 g of dimethylaminoethanol were initially charged with stirring at RT in a 1000 ml four-neck glass flask under an argon atmosphere. 144.4 g of 30% sodium methoxide solution was added dropwise within 15 min. The contents of the flask were heated slowly. At a bottom temperature of 100° C., the solution began to boil (70° C. top temperature). The solution was then heated to 135° C. within 2 h, and the top temperature rose to 125° C. Stirring was then continued at 135° C. for 1 h. 91.8 g of solid p-chlorobenzonitrile were then added at 120° C. The contents of the flask were then stirred at 125° C. for 4 h. The filtrate was concentrated on a rotary evaporator at 70° C. and 20 mbar. The residue was then admixed at RT with 300 ml of water and extracted using 300 ml of toluene. The toluenic solution of benzonitrile obtained in this way was immediately further hydrogenated to benzylamine (cf. Example 6).

Distillative workup of a similar mixture resulted in 4-[2-(dimethylamino)ethoxy]benzonitrile being obtained in a yield of 80.3% (102.9 g) in a GC purity of more than 98% (percentage area).

EXAMPLE 3

15 g of 4-[2-(dimethylamino)ethoxy]benzonitrile (II), 85 g of methanol and 3 g of Raney nickel were installed in a 270 ml pressure autoclave equipped with a sparging stirrer, the autoclave was sealed and inertized using nitrogen. 3 g of ammonia were then injected and the autoclave was heated to an internal temperature of 80° C. At this internal temperature, hydrogen was injected to 65 bar. After 34 min, the hydrogen takeup was complete. Stirring was continued for a further one hour, then the autoclave was cooled to room temperature, decompressed and the ammonia-free reactor effluent was analyzed by means of gas chromatography. The yield of (II) was 99.5%, the selectivity for 4-[2-(dimethylamino)ethoxy]benzylamine was 95.8%.

EXAMPLE 4

The removed catalyst from Example 3 was washed with 100 ml of methanol and reused in the reaction. The procedure was as described in Example 3. After the reaction, the reactor effluent was analyzed by gas chromatography as in Example 3 and the catalyst was washed with 100 ml of methanol and reused in the reaction. The catalyst recycling was repeated five times. The results are compiled in Table 1.

TABLE 1

| Recycling No. | Hydrogen takeup time [min] | Conversion [%] | Selectivity [%] |
|---|---|---|---|
| 1 | 34 | 99.4 | 95.8 |
| 2 | 34 | 99.3 | 96.8 |
| 3 | 38 | 99.1 | 97.3 |
| 4 | 48 | 99.2 | 97.0 |
| 5 | 58 | 99.1 | 97.7 |

EXAMPLE 5

15 g of 4-[2-(dimethylamino)ethoxy]benzonitrile (II), 85 g of methanol and 3 g of Raney nickel were installed in a 270 ml pressure autoclave equipped with a sparging stirrer, the autoclave was sealed and inertized using nitrogen. A certain amount of ammonia (cf. Table 2) was then injected and the autoclave was heated to an internal temperature of 80° C. At this internal temperature, hydrogen was injected to 65 bar. After the end of the hydrogen takeup, stirring was continued for a further one hour, then the autoclave was cooled to room temperature and decompressed, and the ammonia-free reactor effluent was analyzed by gas chromatography. The hydrogen takeup times, conversions and selectivities can be taken from Table 2.

TABLE 2

| Example No. | Amount of ammonia [g] | Hydrogen takeup time [min] | Conversion [%] | Selectivity [%] |
|---|---|---|---|---|
| 5a | 0 | 70 | 99.5 | 81.7 |
| 5b | 3 | 34 | 99.5 | 95.8 |
| 5c | 10 | 13 | 99.9 | 97.6 |

EXAMPLE 6

150 g of the toluenic reaction effluent from Example 2 and 4 g of Raney nickel were installed in a 270 ml pressure autoclave equipped with a sparging stirrer, and the autoclave was sealed and inertized using nitrogen. 15 g of ammonia were then injected and the autoclave was heated to an internal temperature of 80° C. At this internal temperature, hydrogen was injected to 65 bar. After 20 min, the hydrogen takeup was complete. Stirring was continued for a further one hour, then the autoclave was cooled to room temperature and decompressed, and the ammonia-free reactor effluent was analyzed by gas chromatography. The yield of (II) was 99.8%, and the selectivity for 4-[2-(dimethylamino)-ethoxy] benzylamine was 96.0%.

To isolate the product of value, the solvent was removed on a rotary evaporator and the crude product was fractionally distilled via a 20 cm Vigreux column at 10 mbar. The isolated yield of 4-[2-(dimethylamino)ethoxy]benzylamine based on the 4-chlorobenzonitrile used was 82%.

We claim:
1. A process for preparing 4-(aminoalkoxy)benzylamines of general formula (I) by catalytically hydrogenating 4-(aminoalkoxy)benzonitriles of general formula (II)

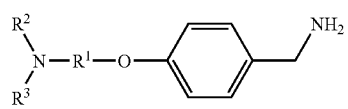

I

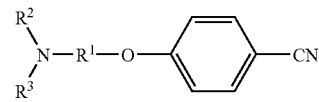

II where, in the compounds of general formula (I) and general formula (II), $R^1$ is $C_1$-$C_8$-alkylene, $R^2$ and $R^3$ are each independently $C_1$-$C_8$-alkyl or are joined to give a ring which may additionally contain a heteroatom, wherein the hydrogenation is conducted at a pressure of from 5 to 350 bar and at a temperature of from 50 to 250° C. and wherein the hydrogenation is conducted in the presence of an organic solvent.

2. A process as claimed in claim 1, wherein the hydrogenation is conducted at pressures of from 5 to 200 bar.

3. A process as claimed in claim 1, wherein the hydrogenation is conducted at temperatures of from 60 to 110° C.

4. A process as claimed in claim 1, wherein the hydrogenation is conducted in the presence of Raney nickel or Raney cobalt.

5. A process as claimed in claim 1, wherein the hydrogenation is conducted in the presence of ammonia.

6. A process as claimed in claim 1, wherein the 4-(aminoalkoxy)benzonitriles of the general formula (II) is obtained by reacting a 4-halobenzonitrile with an alkali metal salt of an aminoalcohol of general formula (III)

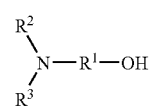

III where $R^1$, $R^2$ and $R^3$ are each as defined above.

7. A process as claimed in claim 6, wherein the alkali metal salt of the aminoalcohol (III) is obtained by reaction with a base AM where M is an alkali metal or an alkaline earth metal and A is hydride, $C_1$-$C_4$-alkyl, hydroxyl or $C_1$-$C_4$-alkoxy.

8. A process as claimed in claim 1, wherein $R^1$ is ethylene and $R^2$ and $R^3$ are each methyl.

9. A process for preparing 4-(aminoalkoxy)benzonitriles of general formula (II)

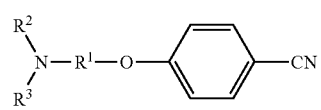

II where $R^1$ is $C_1$-$C_8$-alkylene, and $R^2$ and $R^3$ are each independently $C_1$-$C_8$-alkyl or are joined to give a ring which may additionally contain a heteroatom, the process comprising converting an aminoalcohol of general formula (III) to an alkali metal salt using a base AM where M is an alkali metal or an alkaline earth metal and A is hydride, $C_1$-$C_4$-alkyl, hydroxyl or $C_1$-$C_4$-alkoxy, and reacting the alkali metal salt with 4-halobenzonitrile and wherein the process is conducted in the presence of an aprotic solvent

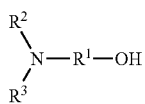

III

10. A process as claimed in claim 9, wherein the base AM is sodium methoxide or sodium ethoxide.

11. A process as claimed in claim 9, wherein methanol or ethanol is distilled out of the reaction mixture.

12. A process as claimed in claim 9, wherein the conversion of the aminoalcohol to the alkali metal salt is conducted at temperatures of from 100 to 140° C.

13. A process as claimed in claim 9, wherein the amount of the alkali metal salt relative to the 4-halobenzonitrile is from 1.00 to 1.5 equivalents.

14. A process as claimed in claim 2, wherein the hydrogenation is conducted at temperatures of from 60 to 110° C.

15. A process as claimed in claim 14, wherein the hydrogenation is conducted in the presence of Raney nickel or Raney cobalt.

16. A process as claimed in claim 14, wherein the hydrogenation is conducted in the presence of ammonia.

17. A process as claimed in claim 14, wherein $R^1$ is ethylene and $R^2$ and $R^3$ are each methyl.

* * * * *